United States Patent
Litvak et al.

(10) Patent No.: US 8,855,344 B2
(45) Date of Patent: *Oct. 7, 2014

(54) DYNAMIC NOISE REDUCTION IN AUDITORY PROSTHESIS SYSTEMS

(71) Applicant: Advanced Bionics AG, Staefa (CH)

(72) Inventors: Leonid M. Litvak, Los Angeles, CA (US); Aniket Saoji, Newhall, CA (US)

(73) Assignee: Advanced Bionics AG, Staefa (CH)

( * ) Notice: Subject to any disclaimer, the term of this patent is extended or adjusted under 35 U.S.C. 154(b) by 34 days.

This patent is subject to a terminal disclaimer.

(21) Appl. No.: 13/720,320

(22) Filed: Dec. 19, 2012

(65) Prior Publication Data

US 2013/0108092 A1    May 2, 2013

Related U.S. Application Data

(63) Continuation of application No. 12/879,623, filed on Sep. 10, 2010, now Pat. No. 8,345,901.

(60) Provisional application No. 61/241,471, filed on Sep. 11, 2009.

(51) Int. Cl.
*H04R 25/00* (2006.01)

(52) U.S. Cl.
CPC .............. *H04R 25/505* (2013.01); *H04R 25/45* (2013.01); *H04R 25/554* (2013.01); *H04R 2225/41* (2013.01); *H04R 2225/67* (2013.01); *H04R 2460/01* (2013.01)
USPC ............................ 381/317; 381/94.3; 381/312

(58) Field of Classification Search
USPC ................ 381/312, 317, 318, 320, 321, 23.1, 381/71.6, 94.1–94.3; 600/559; 607/57
See application file for complete search history.

(56) References Cited

U.S. PATENT DOCUMENTS

| 4,630,305 | A | 12/1986 | Borth et al. |
| 6,757,395 | B1 * | 6/2004 | Fang et al. ................... 381/94.3 |
| 2009/0003627 | A1 * | 1/2009 | Heuermann et al. ......... 381/94.1 |
| 2009/0252358 | A1 * | 10/2009 | Dressler et al. ............... 381/317 |
| 2009/0304203 | A1 * | 12/2009 | Haykin et al. ................ 381/94.1 |

FOREIGN PATENT DOCUMENTS

| EP | 1326479 | 7/2003 |
| EP | 2009955 | 12/2008 |
| GB | 2455824 | 6/2009 |
| WO | WO-2008/116264 | 10/2008 |
| WO | WO-2009/143588 | 12/2009 |

OTHER PUBLICATIONS

International Search Report and Written Opinion received in International Application No. PCT/US2010/048506, dated Dec. 27, 2010.

* cited by examiner

*Primary Examiner* — Tuan D Nguyen
(74) *Attorney, Agent, or Firm* — ALG Intellectual Property, LLC

(57) ABSTRACT

An exemplary method includes a sound processing subsystem 1) dividing an audio signal presented to an auditory prosthesis patient into a plurality of signals each representative of a distinct frequency portion of the audio signal and each contained within a distinct analysis channel included in a plurality of analysis channels, 2) determining a sound level of each signal included in the plurality of signals, and 3) setting an amount of noise reduction applied to each signal included in the plurality of signals in accordance with the determined sound level of each signal included in the plurality of signals. Corresponding methods and systems are also disclosed.

20 Claims, 12 Drawing Sheets

DYNAMIC NOISE REDUCTION IN AUDITORY PROSTHESIS SYSTEMS

RELATED APPLICATIONS

The present application is a continuation application of U.S. patent application Ser. No. 12/879,623, filed Sep. 10, 2010, which claims priority under 35 U.S.C. §119(e) to U.S. Provisional Patent Application No. 61/241,471, filed on Sep. 11, 2009. These applications are incorporated herein by reference in their respective entireties.

BACKGROUND INFORMATION

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

Noise reduction has been shown to be beneficial to cochlear implant patients. However, noise reduction is not always desirable. For example, in quiet environments, noise reduction may result in the patient feeling disconnected from the environment because environmental sounds may not be audible.

SUMMARY

An exemplary method of dynamically adjusting an amount of noise reduction applied in an auditory prosthesis system includes dividing an audio signal presented to an auditory prosthesis patient into a plurality of analysis channels each containing a signal representative of a distinct frequency portion of the audio signal, determining an overall noise level of the signals within the analysis channels, and dynamically adjusting an amount of noise reduction applied to the signals within the analysis channels in accordance with the determined overall noise level. The dynamic adjustment of noise reduction is configured to minimize the amount of noise reduction applied to the signals within the analysis channels if the overall noise level is less than a predetermined minimum threshold.

Another exemplary method of dynamically adjusting an amount of noise reduction applied in an auditory prosthesis system includes dividing an audio signal presented to an auditory prosthesis patient into a plurality of analysis channels each containing a signal representative of a distinct frequency portion of the audio signal, determining an overall noise level of the signals within the analysis channels, minimizing an amount of noise reduction applied to the signals within the analysis channels if the overall noise level is less than a predetermined minimum threshold, and progressively increasing the amount of noise reduction applied to the signals within the analysis channels in response to a progressive increase in the overall noise level above the predetermined minimum threshold.

An exemplary system for dynamically adjusting an amount of noise reduction applied in an auditory prosthesis system includes a frequency analysis facility configured to divide an audio signal into a plurality of analysis channels each containing a signal representative of a distinct frequency portion of the audio signal and a noise reduction facility communicatively coupled to the channel facility. The noise reduction facility is configured to determine an overall noise level of the signals within the analysis channel and dynamically adjust an amount of noise reduction applied to the signals within the analysis channels in accordance with the determined overall noise level. The dynamic adjustment of noise reduction is configured to minimize the amount of noise reduction applied to the signals within the analysis channels if the overall noise level is less than a predetermined minimum threshold.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Methods and systems for dynamically adjusting an amount of noise reduction applied in an auditory prosthesis system are described herein. In some examples, an audio signal presented to an auditory prosthesis patient (e.g., a cochlear implant patient) may be divided into a plurality of analysis channels each containing a signal representative of a distinct frequency portion of the audio signal. An overall noise level of the signals within the analysis channels may then be determined. An amount of noise reduction applied to the signals within the analysis channels may be dynamically adjusted in accordance with the determined overall noise level. As will be described in more detail below, the dynamic adjustment of noise reduction is configured to minimize the amount of noise reduction applied to the signals within the analysis channels if the overall noise level is less than a predetermined minimum threshold. In this manner, a minimal amount of noise reduction may be applied when the patient is located within a relatively quiet environment. The amount of applied noise reduction may be progressively increased in response to a progressive increase in the overall noise level. Such dynamic application of noise reduction to an audio signal may allow an auditory prosthesis patient to perceive environmental sounds present within the quiet environment that would otherwise be rendered imperceptible with noise reduction heuristics used in more noisy environments.

Figure 1:
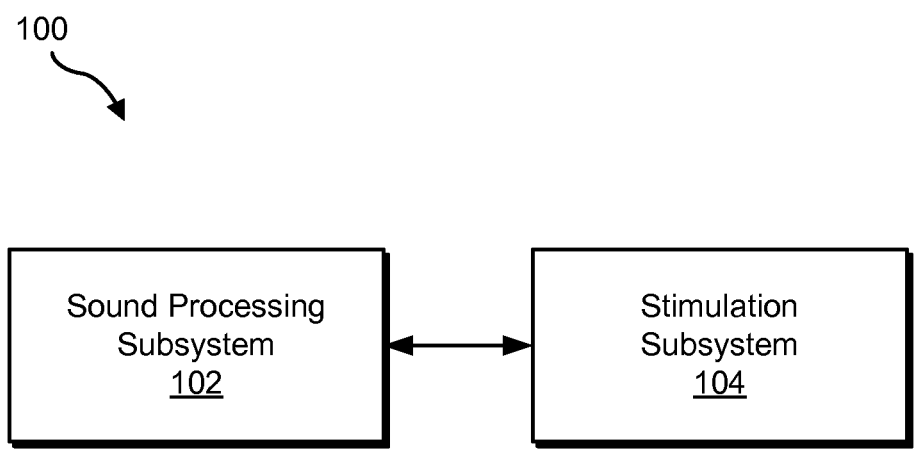
FIG. 1 illustrates an exemplary auditory prosthesis system according to principles described herein.

FIG. 1 illustrates an exemplary auditory prosthesis system 100. As shown in FIG. 1, auditory prosthesis system 100 may include a sound processing subsystem 102 and a stimulation subsystem 104 configured to communicate with one another. As will be described in more detail below, auditory prosthesis system 100 may be configured to determine an overall noise level of an audio signal presented to an auditory prosthesis patient and automatically adjust an amount of noise reduction applied to the audio signal in accordance with the determined noise level.

Sound processing subsystem 102 may be configured to detect or sense an audio signal and divide the audio signal into a plurality of analysis channels each containing a signal representative of a distinct frequency portion of the audio signal. Sound processing subsystem 102 may be further configured to determine an overall noise level of the signals within the analysis channels and dynamically adjust an amount of noise reduction applied to the signals within the analysis channels in accordance with the determined overall noise level. Sound processing subsystem 102 may then transmit one or more stimulation parameters configured to define electrical stimulation representative of the noise-reduced signals to stimulation subsystem 104.

Stimulation subsystem 104 may be configured to generate and apply electrical stimulation (also referred to herein as "stimulation current" and/or "stimulation pulses") to one or more stimulation sites associated with an auditory pathway (e.g., the auditory nerve) of a patient in accordance with one or more stimulation parameters transmitted thereto by sound processing subsystem 102. Exemplary stimulation sites include, but are not limited to, one or more locations within the cochlea, the cochlear nucleus, the inferior colliculus, and/or any other nuclei in the auditory pathway. The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp on time, and ramp off time of the stimulation current that is applied to the stimulation site.

Figure 2:
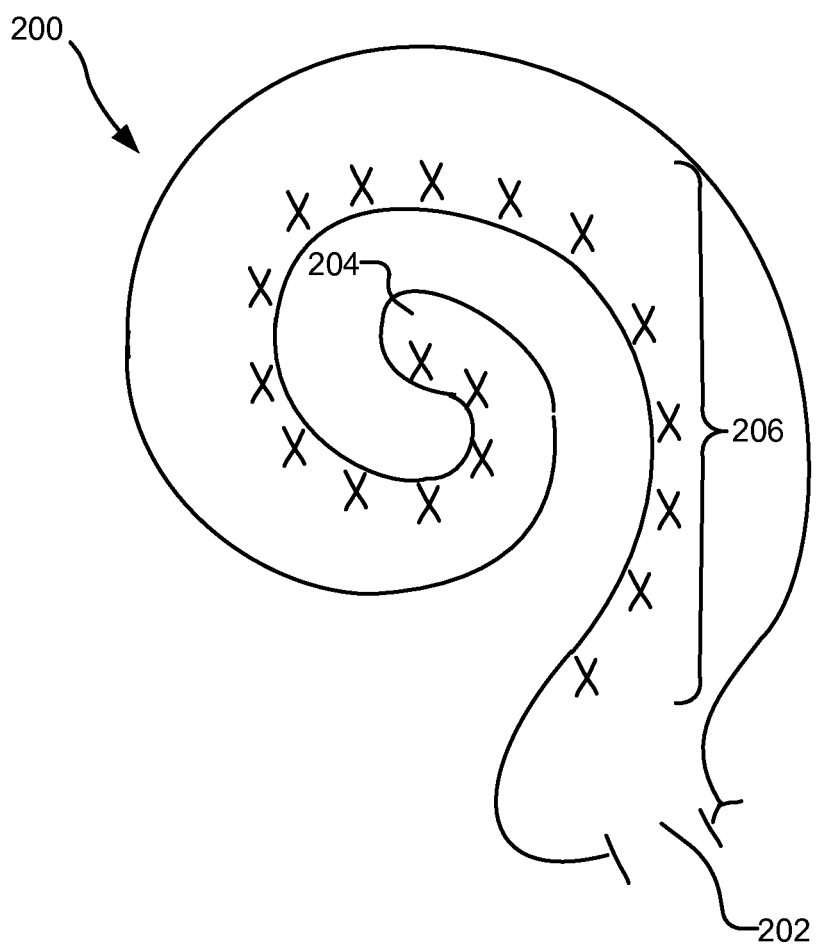
FIG. 2 illustrates a schematic structure of the human cochlea according to principles described herein.

As mentioned, the one or more stimulation sites to which electrical stimulation is applied may include any target area or location within the cochlea. FIG. 2 illustrates a schematic structure of the human cochlea 200. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 104 may therefore be configured to apply electrical stimulation to different locations within the cochlea 200 (e.g., different locations along the auditory nerve tissue 206) to provide a sensation of hearing.

Returning to FIG. 1, sound processing subsystem 102 and stimulation subsystem 104 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application. In some examples, sound processing subsystem 102 may be configured to adjust one or more of these control parameters to facilitate the methods and systems described herein.

Auditory prosthesis system 100, including sound processing subsystem 102 and stimulation subsystem 104, may include any hardware, computer-implemented instructions (e.g., software), firmware, or combinations thereof configured to perform one or more of the processes described herein. For example, auditory prosthesis system 100, including sound processing subsystem 102 and stimulation subsystem 104, may include hardware (e.g., one or more signal processors and/or other computing devices) configured to perform one or more of the processes described herein.

One or more of the processes described herein may be implemented at least in part as instructions executable by one or more computing devices. In general, a processor receives instructions from a computer-readable medium (e.g., a memory, etc.) and executes those instructions, thereby performing one or more processes, including one or more of the processes described herein. Such instructions may be stored and/or transmitted using any of a variety of known computer-readable media.

A computer-readable medium (also referred to as a processor-readable medium) includes any medium that participates in providing data (e.g., instructions) that may be read by a computing device (e.g., by a processor within sound processing subsystem 102). Such a medium may take many forms, including, but not limited to, non-volatile media and/or volatile media. Exemplary computer-readable media that may be used in accordance with the systems and methods described herein include, but are not limited to, random access memory ("RAM"), dynamic RAM, a PROM, an EPROM, a FLASH-EEPROM, any other memory chip or cartridge, or any other medium from which a computing device can read.

Figure 3:
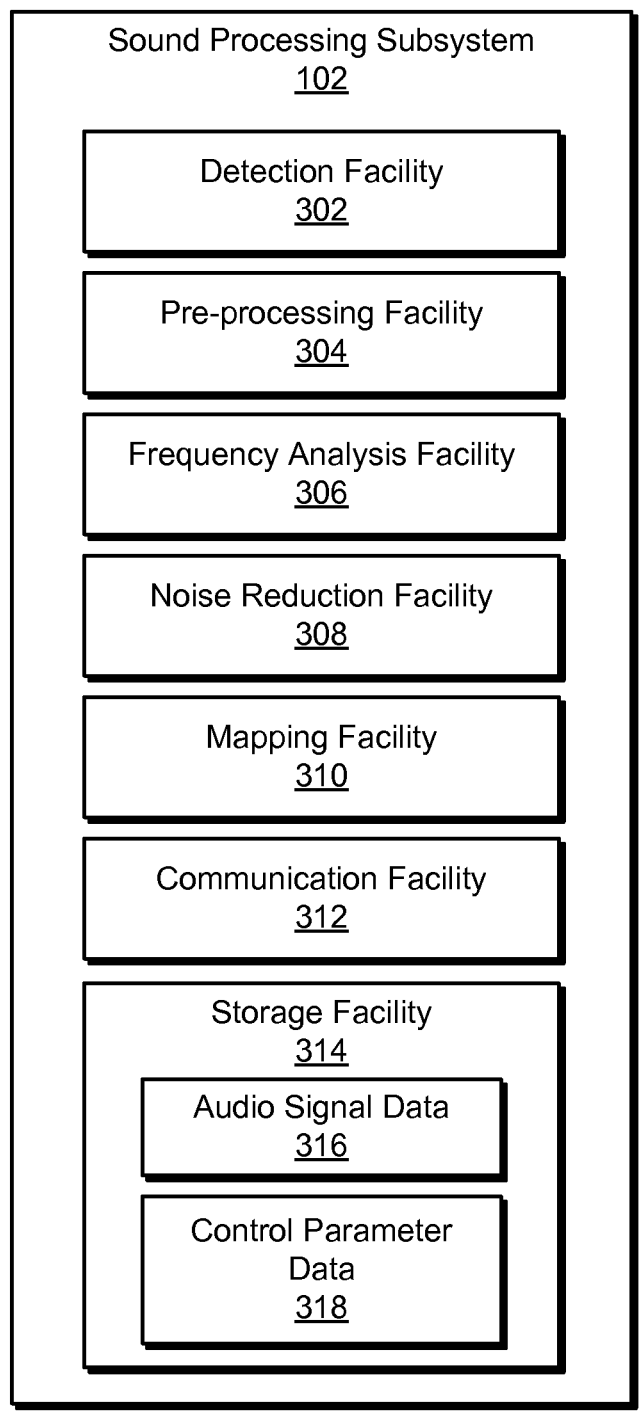
FIG. 3 illustrates exemplary components of a sound processing subsystem according to principles described herein.

FIG. 3 illustrates exemplary components of sound processing subsystem 102. As shown in FIG. 3, sound processing subsystem 102 may include a detection facility 302, a pre-processing facility 304, a frequency analysis facility 306, a noise reduction facility 308, a mapping facility 310, a communication facility 312, and a storage facility 314, which may be in communication with one another using any suitable communication technologies. Each of these facilities 302-314 may include any combination of hardware, software, and/or firmware as may serve a particular application. For example, one or more of facilities 302-314 may include a computing device or processor configured to perform one or more of the functions described herein. Facilities 302-314 will now be described in more detail.

Detection facility 302 may be configured to detect or sense one or more audio signals and convert the detected signals to corresponding electrical signals. To this end, detection facility 302 may include a microphone or other transducer. In some examples, the one or more audio signals may include speech. The one or more audio signals may additionally or alternatively include music, noise, and/or other sounds.

Pre-processing facility 304 may be configured to perform various signal processing operations on the one or more audio signals detected by detection facility 302. For example, pre-processing facility 304 may amplify a detected audio signal, convert the audio signal to a digital signal, filter the digital signal with a pre-emphasis filter, subject the digital signal to automatic gain control, and/or perform one or more other signal processing operations on the detected audio signal.

Frequency analysis facility 306 may be configured to divide the audio signal into a plurality of analysis channels each containing a signal representative of a distinct frequency portion of the audio signal. For example, frequency analysis facility 306 may include a plurality of band-pass filters configured to divide the audio signal into a plurality of frequency channels or bands. Additionally or alternatively, frequency analysis facility 306 may be configured to convert the audio signal from a time domain into a frequency domain and then divide the resulting frequency bins into the plurality of analysis channels. To this end, frequency analysis facility 206 may include one or more components configured to apply a Discrete Fourier Transform (e.g., a Fast Fourier Transform ("FFT")) to the audio signal.

Noise reduction facility 308 may be configured to determine an overall noise level of the signals within the analysis channels and dynamically adjust an amount of noise reduction applied to the signals within the analysis channels in accordance with the determined overall noise level. For example, noise reduction facility 308 may minimize the amount of noise reduction applied to the signals within the analysis channels if the overall noise level is less than a predetermined minimum threshold, progressively increase the amount of noise reduction applied to the signals in response to a progressive increase in the overall noise level above the predetermined minimum threshold, and maintain a maximum amount of noise reduction applied to the signals within the analysis channels if the overall noise level is above a predetermined maximum threshold. Exemplary noise reduction heuristics that may be used in accordance with the systems and methods described herein will be described in more detail below.

Mapping facility 310 may be configured to map the noise reduced signals within the analysis channels to electrical stimulation pulses to be applied to a patient via one or more stimulation channels. For example, signal levels of the noise reduced signals within the analysis channels are mapped to amplitude values used to define electrical stimulation pulses that are applied to the patient by stimulation subsystem 104 via one or more corresponding stimulation channels. Mapping facility 310 may be further configured to perform additional processing of the signals contained within the analysis channels, such as signal compression.

Communication facility 312 may be configured to facilitate communication between sound processing subsystem 102 and stimulation subsystem 104. For example, communication facility 312 may include one or more coils configured to transmit control signals and/or power via one or more communication links to stimulation subsystem 104. Additionally or alternatively, communication facility 312 may one or more wires or the like that are configured to facilitate direct communication with stimulation subsystem 104.

Storage facility 314 may be configured to maintain audio signal data 316 representative of an audio signal detected by detection facility 302 and control parameter data 318 representative of one or more control parameters, which may include one or more stimulation parameters to be transmitted from sound processing subsystem 102 to stimulation subsystem 104. Storage facility 314 may be configured to maintain additional or alternative data as may serve a particular application.

Figure 4:
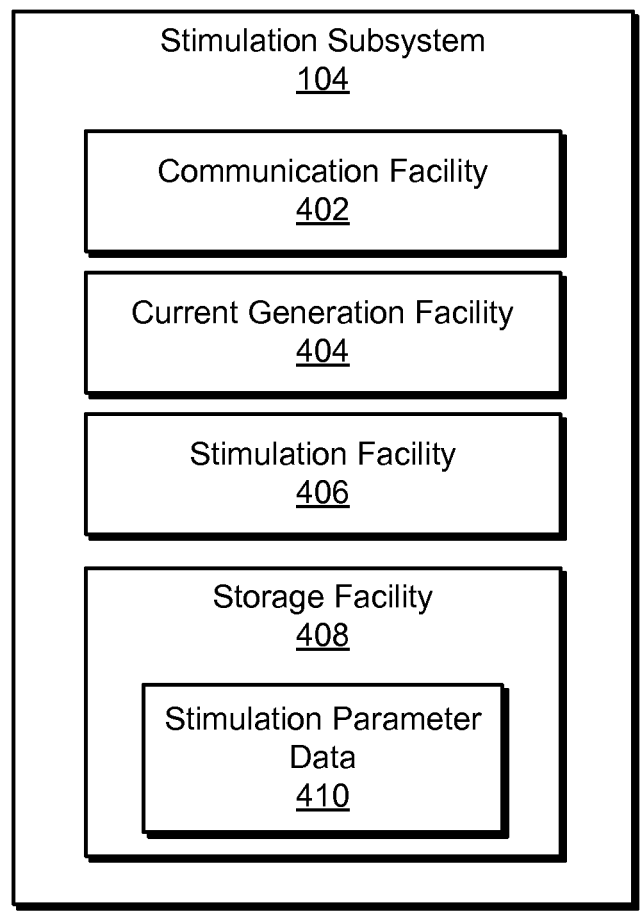
FIG. 4 illustrates exemplary components of a stimulation subsystem according to principles described herein.

FIG. 4 illustrates exemplary components of stimulation subsystem 104. As shown in FIG. 4, stimulation subsystem 104 may include a communication facility 402, a current generation facility 404, a stimulation facility 406, and a storage facility 408, which may be in communication with one another using any suitable communication technologies. Each of these facilities 402-408 may include any combination of hardware, software, and/or firmware as may serve a particular application. For example, one or more of facilities 402-408 may include a computing device or processor configured to perform one or more of the functions described herein. Facilities 402-408 will now be described in more detail.

Communication facility 402 may be configured to facilitate communication between stimulation subsystem 104 and sound processing subsystem 102. For example, communication facility 402 may include one or more coils configured to receive control signals and/or power via one or more communication links to stimulation subsystem 104. Communication facility 402 may additionally or alternatively be configured to transmit one or more status signals and/or other data to sound processing subsystem 102.

Current generation facility 404 may be configured to generate electrical stimulation in accordance with one or more stimulation parameters received from sound processing subsystem 102. To this end, current generation facility 404 may include one or more current generators and/or any other circuitry configured to facilitate generation of electrical stimulation.

Stimulation facility 406 may be configured to apply the electrical stimulation generated by current generation facility 404 to one or more stimulation sites within the cochlea of a patient. To this end, as will be illustrated in more detail below, stimulation facility 406 may include one or more electrodes disposed on a lead that may be inserted within the cochlea, into one or more nuclei in the auditory pathway (e.g., into the cochlear nucleus and/or the inferior colliculus), and/or at any other location along the auditory pathway.

Storage facility 408 may be configured to maintain stimulation parameter data 410 as received from sound processing subsystem 102. Stimulation parameter data 410 may be representative of one or more stimulation parameters configured to define the electrical stimulation generated and applied by stimulation subsystem 104. Storage facility 408 may be configured to maintain additional or alternative data as may serve a particular application.

Figure 5:
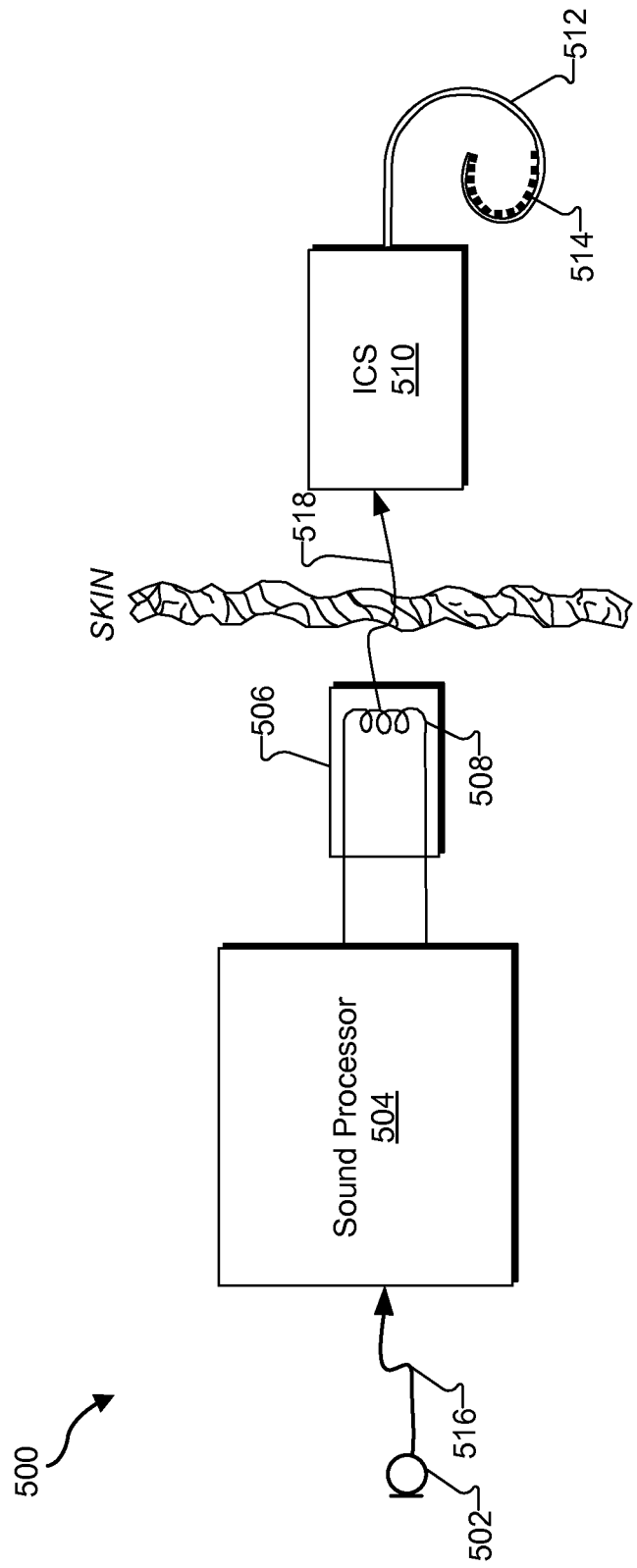
FIG. 5 illustrates an exemplary cochlear implant system according to principles described herein.

FIG. 5 illustrates an exemplary cochlear implant system 500, which may implement auditory prosthesis system 100. It will be recognized that cochlear implant system 500 is one of many different types of systems that may implement auditory prosthesis system 100. For example, in some alternative implementations, a brainstem implant and/or any other type of auditory prosthesis may be implanted within a patient and configured to apply stimulation to one or more stimulation sites located along an auditory pathway of a patient.

As shown in FIG. 5, cochlear implant system 500 may include a microphone 502, a sound processor 504, a headpiece 506 having a coil 508 disposed therein, an implantable cochlear stimulator ("ICS") 510, a lead 512, and a plurality of electrodes 514 disposed on the lead 512. Additional or alternative components may be included within cochlear implant system 500 as may serve a particular application. The facilities described herein may be implemented by or within one or more components shown within FIG. 5. For example, detection facility 302 may be implemented by microphone 502. Pre-processing facility 304, frequency analysis facility 306, noise reduction facility 308, mapping facility 310, and/or storage facility 314 may be implemented by sound processor 504. Communication facility 312 may be implemented by headpiece 506 and coil 508. Communication facility 402, current generation facility 404, and storage facility 408 may be implemented by implantable cochlear stimulator 508. Stimulation facility 406 may be implemented by lead 510 and electrodes 512.

As shown in FIG. 5, microphone 502, sound processor 504, and headpiece 506 may be located external to a patient. In some alternative examples, microphone 502 and/or sound processor 504 may be implanted within the patient. In such configurations, the need for headpiece 506 may be obviated.

Microphone 502 may detect an audio signal and convert the detected signal to a corresponding electrical signal. Microphone 502 may be placed external to the patient, within the ear canal of the patient, or at any other suitable location as may serve a particular application. The electrical signal may be sent from microphone 502 to sound processor 504 via a communication link 514, which may include a telemetry link, a wire, and/or any other suitable communication link.

Sound processor 504 is configured to process the converted audio signal in accordance with a selected sound processing strategy to generate appropriate stimulation parameters for controlling implantable cochlear stimulator 510. Sound processor 504 may include or be implemented within a behind-the-ear ("BTE") unit, a portable speech processor ("PSP"), and/or any other sound processing unit as may serve a particular application. Exemplary components of sound processor 504 will be described in more detail below.

Sound processor 504 may be configured to transcutaneously transmit data (e.g., data representative of one or more stimulation parameters) to implantable cochlear stimulator 504 via coil 508. As shown in FIG. 5, coil 508 may be housed within headpiece 506, which may be affixed to a patient's head and positioned such that coil 508 is communicatively coupled to a corresponding coil (not shown) included within implantable cochlear stimulator 510. In this manner, data may be wirelessly transmitted between sound processor 504 and implantable cochlear stimulator 510 via communication link 518. It will be understood that data communication link 118 may include a bi-directional communication link and/or one or more dedicated uni-directional communication links. In some alternative embodiments, sound processor 504 and implantable cochlear stimulator 510 may be directly connected with one or more wires or the like.

Implantable cochlear stimulator 510 may be configured to generate electrical stimulation representative of an audio signal detected by microphone 502 in accordance with one or more stimulation parameters transmitted thereto by sound processing subsystem 102. Implantable cochlear stimulator 510 may be further configured to apply the electrical stimulation to one or stimulation sites within the cochlea via one or more electrodes 514 disposed along lead 512.

To facilitate application of the electrical stimulation generated by implantable cochlear stimulator 510, lead 512 may be inserted within a duct of the cochlea such that electrodes 514 are in communication with one or more stimulation sites within the cochlea. As used herein, the term "in communication with" refers to electrodes 514 being adjacent to, in the general vicinity of, in close proximity to, directly next to, or directly on the stimulation site. Any number of electrodes 514 (e.g., sixteen) may be disposed on lead 512 as may serve a particular application.

Figure 6:
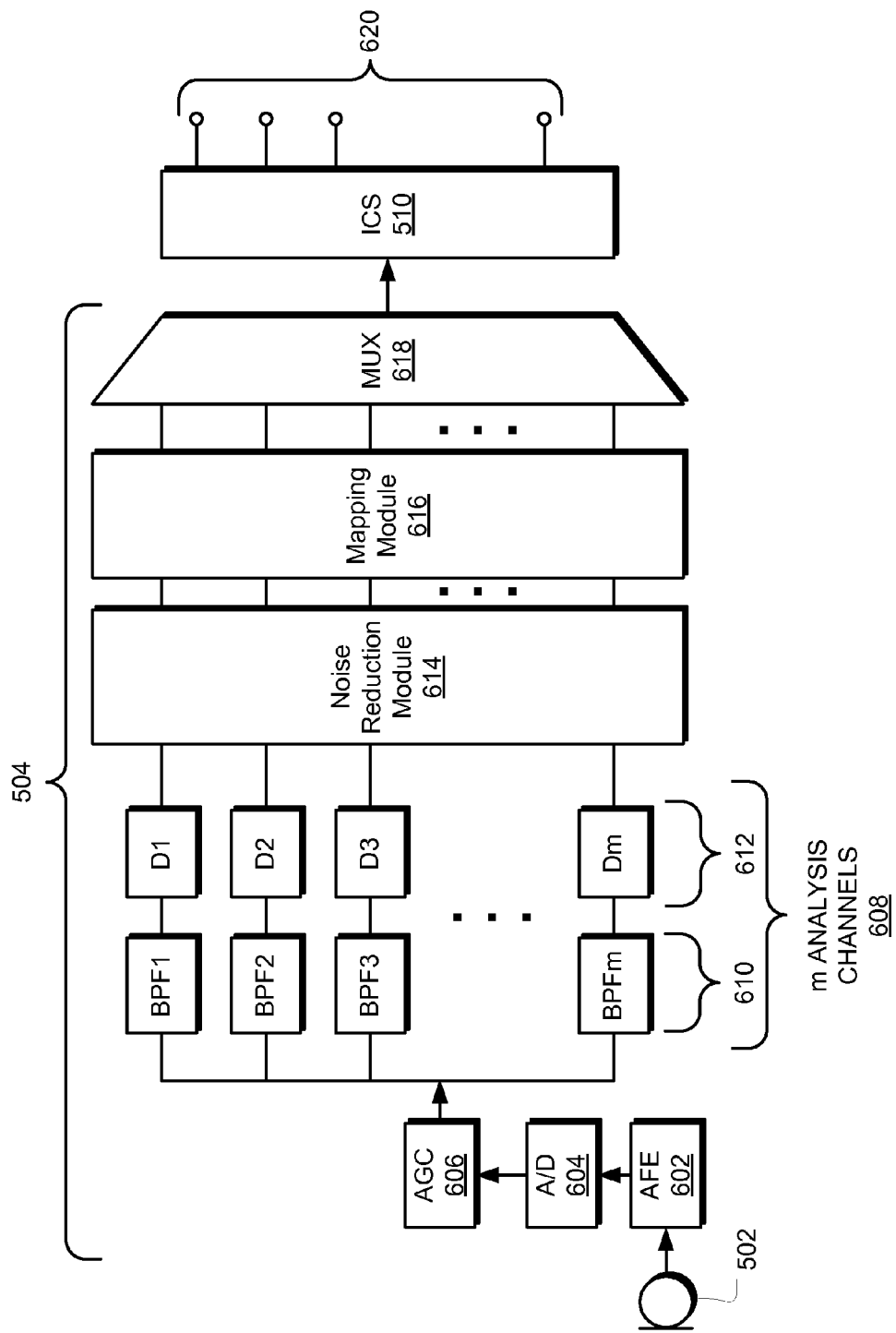
FIG. 6 illustrates components of an exemplary sound processor coupled to an implantable cochlear stimulator according to principles described herein.

FIG. 6 illustrates components of an exemplary sound processor 504 coupled to an implantable cochlear stimulator 510. The components shown in FIG. 6 may be configured to perform one or more of the processes associated with one or more of the facilities 302-314 associated with sound processing subsystem 102 and are merely representative of the many different components that may be included within sound processor 504.

As shown in FIG. 6, microphone 502 senses an audio signal, such as speech or music, and converts the audio signal into one or more electrical signals. These signals are then amplified in audio front-end ("AFE") circuitry 602. The amplified audio signal is then converted to a digital signal by an analog-to-digital ("A/D") converter 604. The resulting digital signal is then subjected to automatic gain control using a suitable automatic gain control ("AGC") unit 606.

After appropriate automatic gain control, the digital signal is subjected to a plurality of filters 610 (e.g., a plurality of band-pass filters). Filters 610 are configured to divide the digital signal into m analysis channels 608 each containing a signal representative of a distinct frequency portion of the audio signal sensed by microphone 502. Additional or alternative components may be used to divide the signal into the analysis channels 608 as may serve a particular application. For example, as described previously, one or more components may be included within sound processor 504 that are configured to apply a Discrete Fourier Transform to the audio signal and then divide the resulting frequency bins into the analysis channels 608.

As shown in FIG. 6, the signals within each analysis channel 608 may be input into an energy detector 612. Each energy detector 612 may include any combination of circuitry configured to detect an amount of energy contained within each of the signals within the analysis channels 608. For example, each energy detector 612 may include a rectification circuit followed by an integrator circuit.

After energy detection, the signals within the m analysis channels 608 are input into a noise reduction module 614. Noise reduction module 614 may perform one or more of the functions described in connection with noise reduction facility 308. For example, noise reduction module 614 may determine an overall noise level of the signals within the analysis channels and dynamically adjust an amount of noise reduction applied to the signals within the analysis channels in accordance with the determined overall noise level. Noise reduction module 614 will be described in more detail below.

Mapping module 616 may perform one or more of the functions described in connection with mapping facility 310. For example, mapping module 616 may map the signals in the analysis channels 608 to one or more stimulation channels after the signals have been subjected to noise reduction by noise reduction module 614. For example, signal levels of the noise reduced signals included within the m analysis channels 608 are mapped to amplitude values used to define the electrical stimulation pulses that are applied to the patient by implantable cochlear stimulator 510 via M stimulation channels 620. In some examples, groups of one or more electrodes 514 may make up the M stimulation channels 620.

The mapped signals may be serialized by a multiplexer 618 and transmitted to implantable cochlear stimulator 510. The implantable cochlear stimulator 510 may then apply electrical stimulation via one or more of the M stimulation channels 620 to one or more stimulation sites within the duct of the patient's cochlea.

Figure 7:
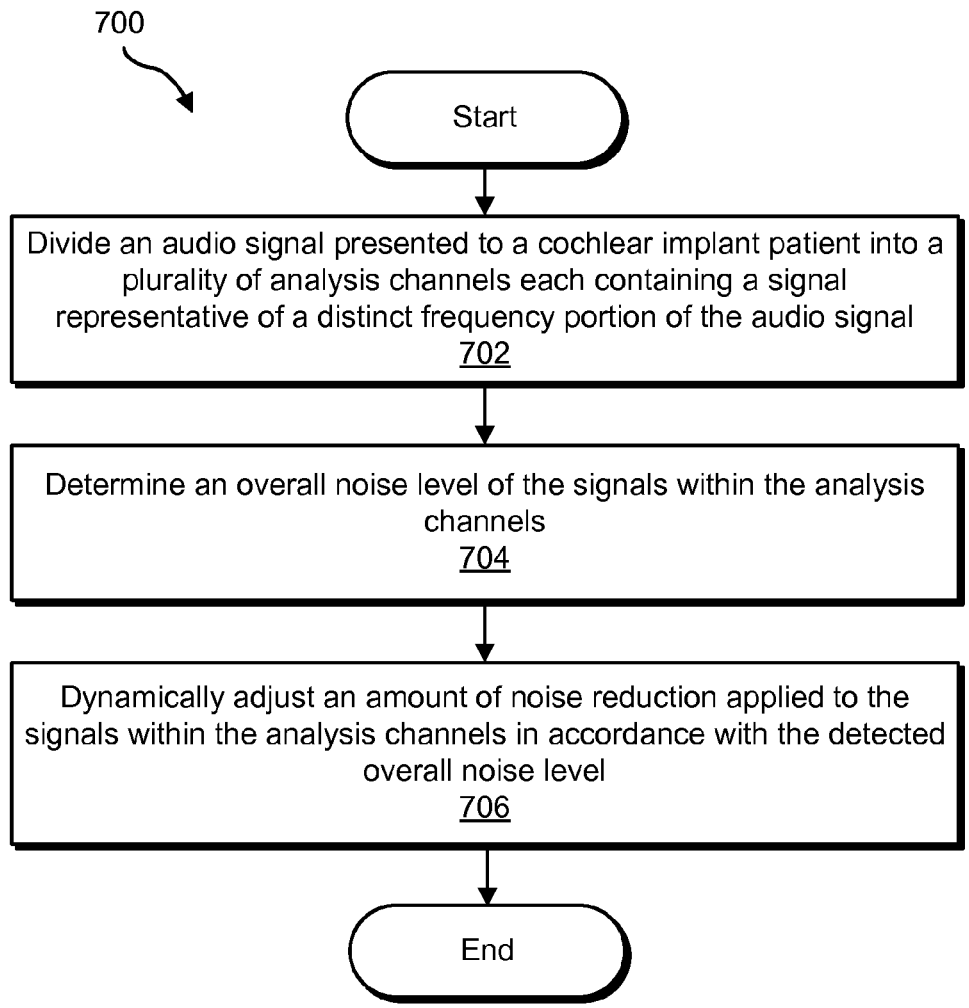
FIG. 7 illustrates an exemplary dynamic noise reduction method according to principles described herein.

FIG. 7 illustrates an exemplary dynamic noise reduction method 700 that may be used in an auditory prosthesis system. While FIG. 7 illustrates exemplary steps according to one embodiment, other embodiments may omit, add to, reorder, and/or modify any of the steps shown in FIG. 7. It will be recognized that any of the systems, subsystems, facilities, and/or modules may be configured to perform one or more of the steps shown in FIG. 7.

In step 702, an audio signal presented to an auditory prosthesis patient is divided into a plurality of analysis channels each containing a signal representative of a distinct frequency portion of the audio signal. Step 702 may be performed by frequency analysis facility 306, for example, in any of the ways described herein.

Figure 8:
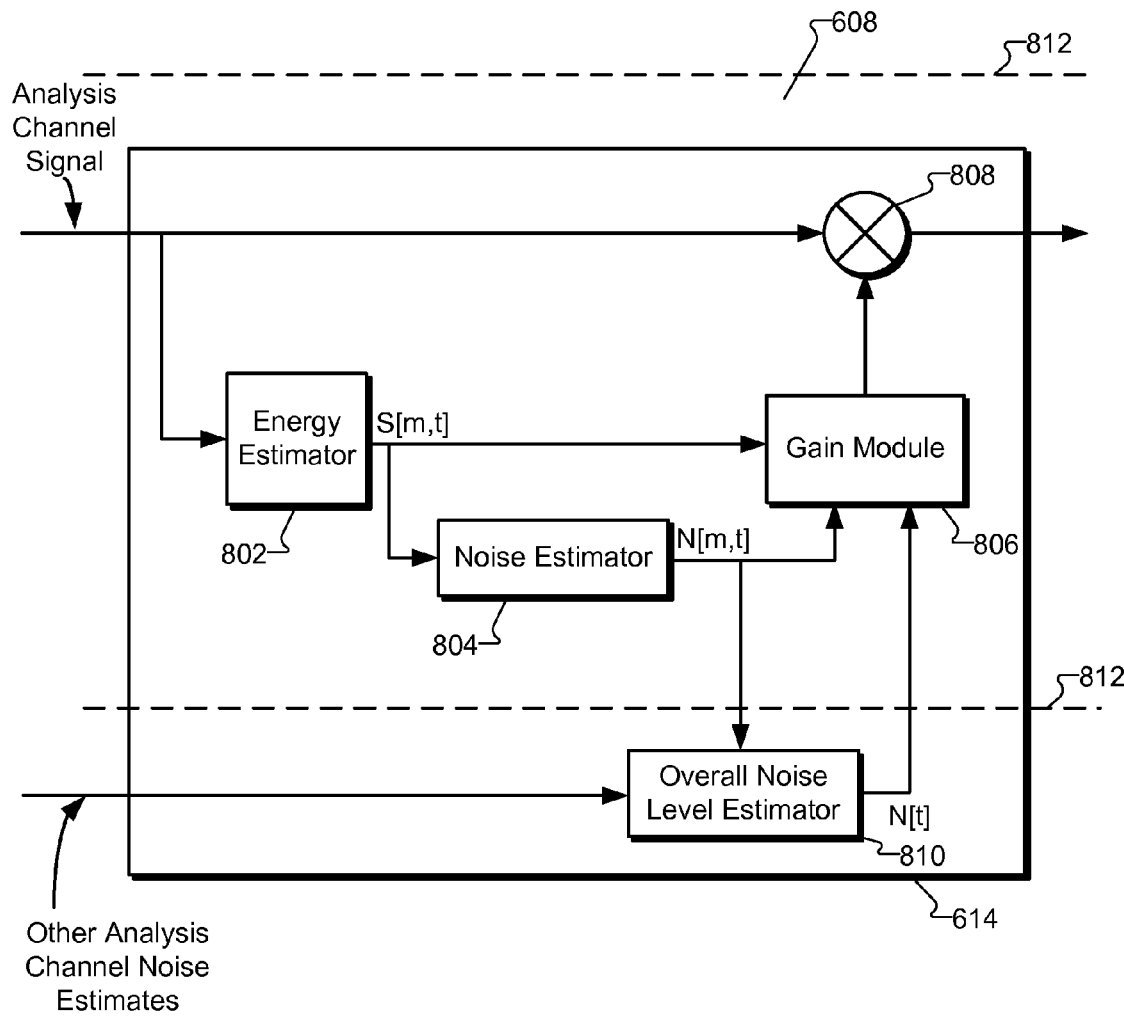
FIG. 8 shows exemplary components that may be included within a noise reduction module that may be used to determine the overall noise level of the signals within a plurality of analysis channels according to principles described herein.

In step 704, an overall noise level of the signals within the analysis channels is determined. To illustrate, FIG. 8 shows exemplary components that may be included within noise reduction module 614 that may be used to determine the overall noise level of the signals within analysis channels 608 shown in FIG. 6. As shown in FIG. 8, noise reduction module 614 may include an energy estimator 802, a noise estimator 804, a gain module 806, a summation block 808, and an overall noise level estimator 810 communicatively coupled to one another.

Energy estimator 802, noise estimator 804, gain module 806, and summation block 808 are included within dashed lines 812 to illustrate that they are specific to a particular analysis channel 608. Hence, in some examples, each of these components 802-808 may be replicated for each analysis channel 608. In some examples, a single component (e.g., a digital signal processor) or combination of components may be configured to perform the functions associated with each of the components 802-808 for each of the signals contained within analysis channels 608.

As shown in FIG. 8, energy estimator 802 may be configured to estimate or otherwise determine an energy level of a signal contained within a particular analysis channel 608. The energy level may be estimated in any suitable manner as may serve a particular application. The energy level of the signal contained within analysis channel 608 may be represented as S[m,t], where m represents the particular analysis channel number and t represents time. Hence, S[m,t] represents the energy level estimate of the signal in channel m at time t.

The estimated energy level is input into noise estimator 804, which analyzes the estimated energy level to determine an estimated noise level of the signal. The estimated noise level may be determined in any suitable manner as may serve a particular application and may be represented as N[m,t], where m represents the particular analysis channel number and t represents time. Hence, N[m,t] represents the noise level estimate in channel m at time t. For example, N[m,t] may be estimated by detecting stationary steady components in the signal S[m,t]. Alternatively, noise may be estimating by measuring signal S[m,t] during absence of speech, as cued by a voice activity detector circuit.

Gain module 806 may be configured to accept both S[m,t] and N[m,t] and take the ratio thereof to determine a signal-to-noise ratio ("SNR") of the signal contained within analysis channel 608, which may be represented by SNR[m,t]. As will be described in more detail below, gain module 806 may use SNR[m,t] in combination with an overall noise level value as determined by overall noise level estimator 810 to determine an appropriate gain to be applied to the signal contained within analysis channel 608. In some examples, the gain is applied to the signal via summation block 808.

As shown in FIG. 8, N[m,t] may also be input into overall noise level estimator 810. Overall noise level estimator 810 may additionally receive noise level estimates of each of the other analysis channels and compute the overall noise level of the signals contained within the analysis channels in accordance with Equation 1:

$$N[t] = \sqrt{\sum_m N[m, t]^2} \quad \text{(Equation 1)}$$

Overall noise level estimator 810 may be further configured to integrate N[t] over time in accordance with Equation 2:

$$Ns[t] = \alpha * Ns[t-1] + (1-\alpha) * Ns[t] \quad \text{(Equation 2)}$$

Returning to FIG. 7, in step 706, an amount of noise reduction applied to the signals within the analysis channels is dynamically adjusted in accordance with the overall noise level as determined in step 704. The amount of noise reduction applied to the signals within the analysis channels may be dynamically adjusted by adjusting an amount of gain applied to the signals with gain module 806. For example, gain module 806 may be configured to adjust an amount of gain applied to the signal in accordance with the overall noise level of the signals within analysis channels 608. The amount of gain may be adjusted in any suitable manner as may serve a particular application. For example, gain module 806 may be configured to compute the gain per analysis channel according to Equation 3:

$$G[m,t] = G(SNR[m,t])^{C(Ns[t])} \quad \text{(Equation 3)}$$

In Equation 3, G(SNR[m,t]) represents the gain determined by gain module 806 without the additional input of N[t]. C(Ns[t]) represents a correction to the gain determination that is based on the overall noise level of the signals contained within the analysis channels 608. C(Ns[t]) is typically equal to zero below a predetermined minimum threshold (e.g., 25 dB SPL). In such instances, G[m,t] is always equal to one. In other words, noise reduction is minimized when C(Ns[t]) is equal to zero.

C(Ns[t]) is typically equal to one above a predetermined maximum threshold (e.g., 40 dB SPL). In such instances, full gain (i.e., maximum noise reduction) is applied to the signals contained within the analysis channels 608. In between the predetermined minimum and maximum threshold levels, C(Ns[t]) may be linear function of Ns[t].

In this manner, the amount of noise reduction applied to the signals contained within analysis channels 608 may be minimized if the overall noise level N[t] is less than the predetermined minimum threshold, progressively increased in response to a progressive increase in the overall noise level N[t] above the predetermined minimum threshold, and maintained at a maximum amount if the overall noise level N[t] is above a predetermined maximum threshold. Hence, in quiet environments where the overall noise level N[t] is less than the predetermined minimum threshold, noise reduction module 614 may cease applying noise reduction to detected audio signals or otherwise minimize the amount of noise reduction applied to detected audio signals so that the patient can perceive environmental sounds.

Additionally or alternatively, noise reduction module 614 may be configured to dynamically adjust an amount of noise reduction applied to the signals within analysis channels 608 by adjusting one or more parameters used by mapping module 616 to map the signals to electrical stimulation pulses to be applied to a patient via one or more stimulation channels 620.

Figure 9:
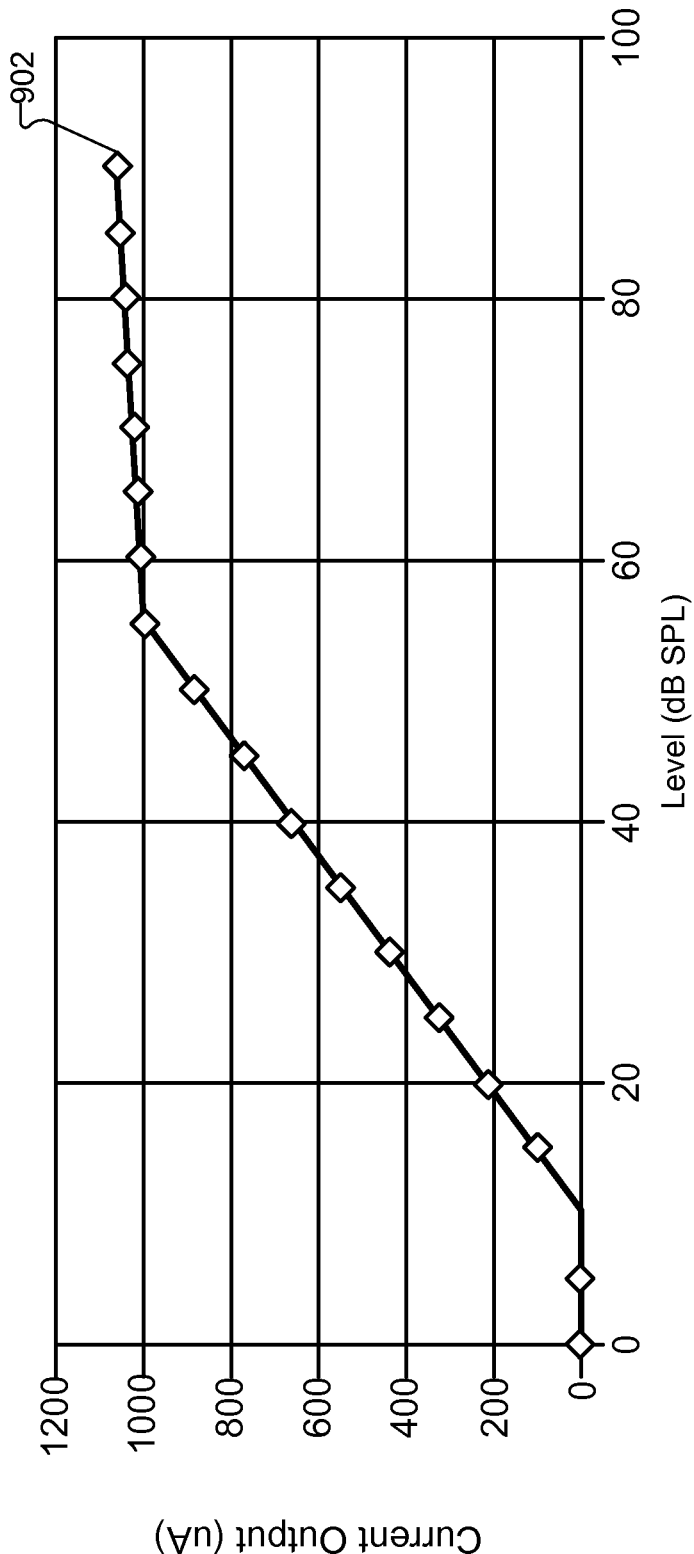
FIGS. 9-11 illustrate exemplary mapping functions according to principles described herein.

To illustrate, FIG. 9 shows a curve 902 (shown with diamonds disposed thereon for illustrative purposes) that represents an exemplary mapping function that may be used by mapping module 616 in the absence of noise reduction to map loudness levels of the signals contained within analysis channels 608 to amplitudes of stimulation pulses used to represent the signals when applied to a patient. The mapping function may be defined by a T level, an M level, and a dynamic range (also referred to herein as an "input dynamic range" or "IDR"). The T level represents a minimum amplitude of stimulation current which when applied to a given electrode associated with the channel produces a sensed perception of sound. The M level represents a most comfortable amplitude of stimulation current which when applied to the given electrode produces a sensed perception of sound that is moderately loud, or comfortably loud, but not so loud that the perceived sound is uncomfortable. The sound amplitude associated with M level stimulation is set to a suitable value (e.g., 55 dB SPL). The sound amplitude associated with T level stimulation is equal to the sound amplitude associated with M level stimulation minus the IDR. In other words, IDR represents the difference (in SPL) between sound amplitude producing T level stimulation and sound amplitude producing M level stimulation.

The T and M levels are specific to a particular patient. For example, a T level associated with a particular patient may be equal to 200 microamps and a M level associated with the particular patient may be equal to 1000 microamps. As shown in FIG. 9, The T level may be mapped to any suitable loudness level (e.g., 20 dB SPL). Likewise, the M level may be mapped to any suitable loudness level (e.g., 60 dB SPL).

Figure 10:
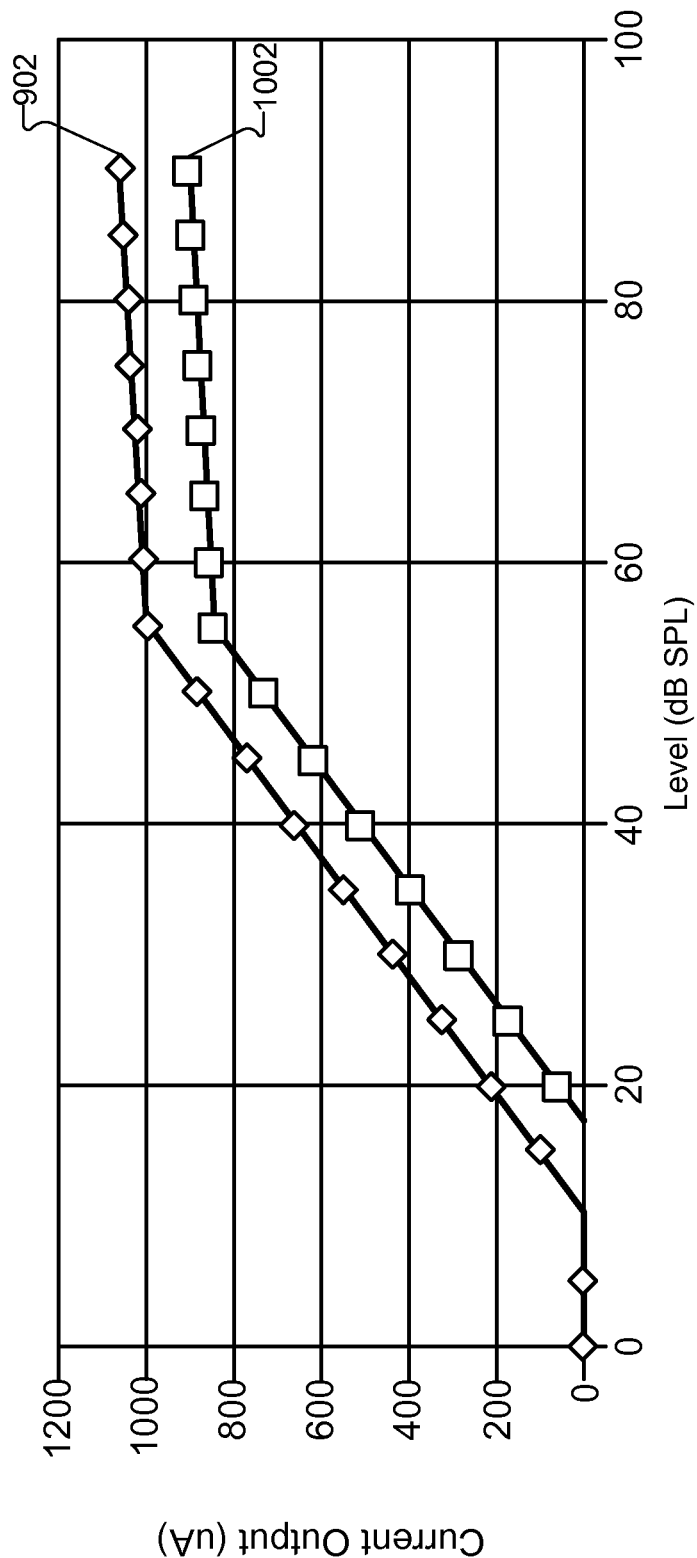

FIG. 10 shows another curve 1002 (shown with squares disposed thereon for illustrative purposes) that illustrates an effect on the mapping function associated with curve 902 of applying 10 dB of attenuation to all signal levels. The mapping function illustrated by curve 1002 corresponds to a configuration where noise reduction is applied uniformly to all loudness levels as opposed to being dynamically adjusted depending on the particular noise level. As shown in FIG. 10, curve 1002 is uniformly shifted down. Such a shift may result in some low level signals being attenuated below the patient's T level (e.g., 20 dB SPL), thus resulting in the patient not being able to perceive sounds at these levels.

In some examples, noise reduction module 614 may be configured to dynamically adjust an amount of noise reduction applied to the signals within analysis channels 608 by increasing the T level of a patient to match the predetermined minimum threshold below which noise reduction is minimized. Additionally or alternatively, noise reduction module 614 may be configured to dynamically adjust an amount of noise reduction applied to the signals within analysis channels 608 by increasing the dynamic range.

Figure 11:
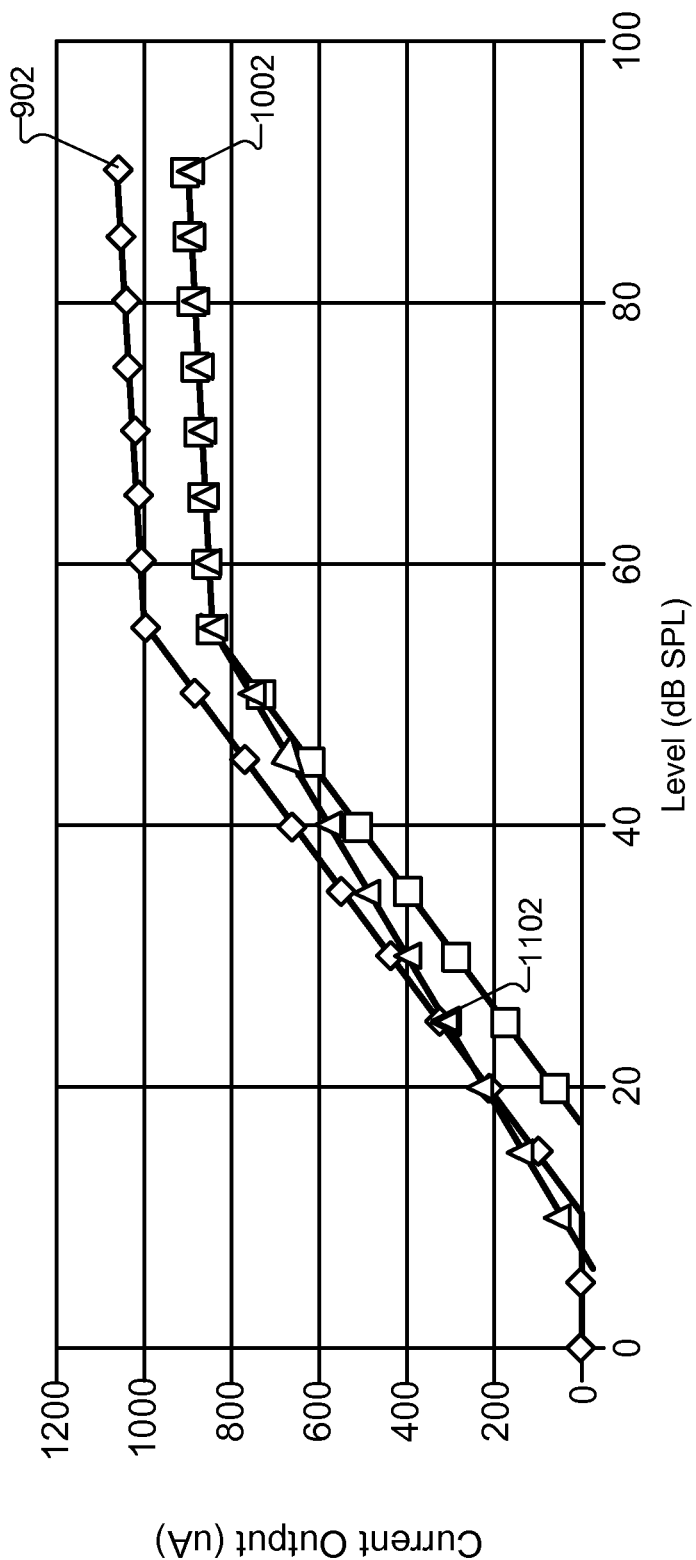

For example, FIG. 11 shows another curve 1102 (shown with triangles disposed thereon for illustrative purposes) representative of a mapping function using noise reduction described in connection with FIG. 10 after the dynamic range has been increased by 10 dB. As shown in FIG. 11, the increase in dynamic range effectively decreases the slope of curve 1102, thereby preventing relatively lower level signals from being attenuated and at the same time allowing relatively higher level signals to be attenuated. An increase in the T level may similarly decrease the slope of curve 1102.

As a further illustration, suppose that a particular mapping function has a M level corresponding to 60 dB SPL and a T level corresponding to 60-IDR. In between these two values, the mapping may be linear. Thus, for any level A, the mapping function may be represented by MAP(A), which may be equal to (M−T)/IDR*(A−60+IDR)+T. Suppose that A is the ambiance level in a quiet room (e.g. 25 dB SPL). To derive a new mapping function MAPnew(A), where MAP(A)=MAPnew(A−Nr), T may be changed in the new function as follows: Tnew=M*Nr/(Nr+Ad)+T*Ad/(Nr+Ad). In this equation, Ad=60−A and Nr is the amount in dB by which ambient noise is attenuated by noise reduction.

In some examples, the predetermined minimum threshold below which noise reduction is minimized may set to substantially equal a T level of a particular patient. Likewise, the predetermined maximum threshold above which a maximum amount of noise reduction is maintained may be set to substantially equal a M level of a particular patient. It will be recognized that the predetermined minimum and maximum thresholds may be set to equal any value as may serve a particular application and that they may vary from patient to patient.

In some examples, the T level of a particular patient may be automatically and/or manually adjusted during a fitting session. For example, a clinician may present a variety of environmental sounds to a patient during a fitting session and adjust a T level parameter associated with the patient until the thresholds are audible to the patient.

In some examples, the release of noise reduction is coordinated with the action of the AGC unit 606. In this manner, the effect on patient perception of dynamic application of noise reduction may be minimized. For example, an amount of noise reduction applied to signals within analysis channels may be decreased during a time frame associated with a release of gain of the AGC unit 606.

Figure 12:
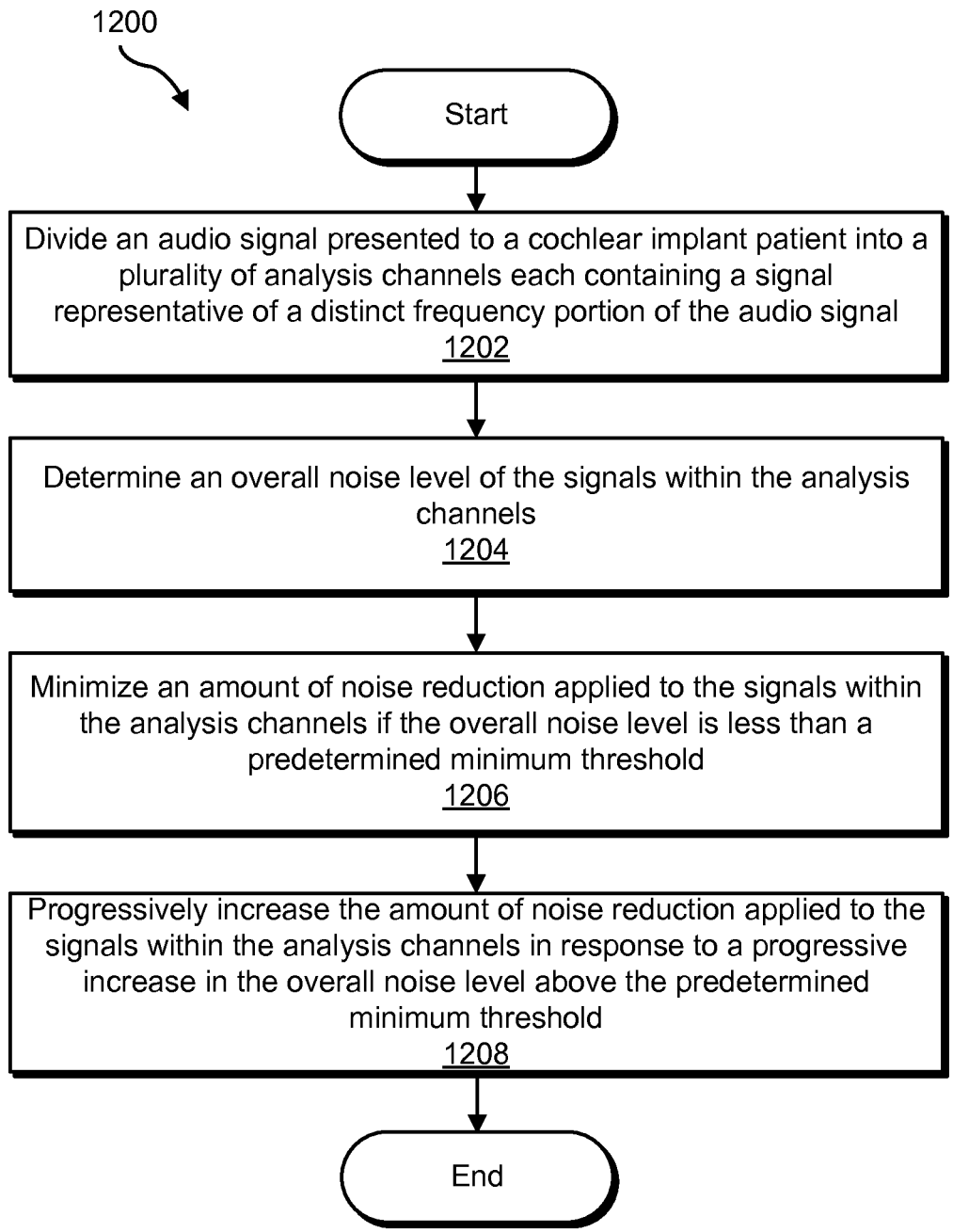
FIG. 12 illustrates another exemplary dynamic noise reduction method according to principles described herein.

FIG. 12 illustrates another exemplary dynamic noise reduction method 1200 that may be used in an auditory prosthesis system. While FIG. 12 illustrates exemplary steps according to one embodiment, other embodiments may omit, add to, reorder, and/or modify any of the steps shown in FIG. 12. It will be recognized that any of the systems, subsystems, facilities, and/or modules may be configured to perform one or more of the steps shown in FIG. 12.

In step 1202, an audio signal presented to an auditory prosthesis patient is divided into a plurality of analysis channels each containing a signal representative of a distinct frequency portion of the audio signal. Step 1202 may be performed by frequency analysis facility 306, for example, in any of the ways described herein.

In step 1204, an overall noise level of the signals within the analysis channels is determined. The overall noise level may be determined in any of the ways described herein.

In step 1206, an amount of noise reduction applied to the signals within the analysis channels is minimized if the overall noise level is less than a predetermined minimum threshold. The amount of noise reduction may be minimized in any of the ways described herein.

In step 1208, the amount of noise reduction applied to the signals within the analysis channels is progressively increased in response to a progressive increase in the overall noise level above the predetermined minimum threshold. The noise reduction may be progressively increased in any of the ways described herein.

As detailed above, the methods and systems described herein facilitate dynamic noise reduction in auditory prosthesis systems. As an example, an exemplary method includes dividing an audio signal presented to an auditory prosthesis patient into a plurality of analysis channels each containing a signal representative of a distinct frequency portion of the audio signal, determining an overall noise level of the signals within the analysis channels, and dynamically adjusting an amount of noise reduction applied to the signals within the analysis channels in accordance with the determined overall noise level. The dynamic adjustment of noise reduction is configured to minimize the amount of noise reduction applied to the signals within the analysis channels if the overall noise level is less than a predetermined minimum threshold.

Another exemplary method includes dividing an audio signal presented to an auditory prosthesis patient into a plurality of analysis channels each containing a signal representative of a distinct frequency portion of the audio signal, determining an overall noise level of the signals within the analysis channels, minimizing an amount of noise reduction applied to the signals within the analysis channels if the overall noise level is less than a predetermined minimum threshold, and progressively increasing the amount of noise reduction applied to the signals within the analysis channels in response to a progressive increase in the overall noise level above the predetermined minimum threshold.

An exemplary system includes a frequency analysis facility configured to divide an audio signal into a plurality of analysis channels each containing a signal representative of a distinct frequency portion of the audio signal and a noise reduction facility communicatively coupled to the channel facility. The noise reduction facility is configured to determine an overall noise level of the signals within the analysis channel and dynamically adjust an amount of noise reduction applied to the signals within the analysis channels in accordance with the determined overall noise level. The dynamic adjustment of noise reduction is configured to minimize the amount of noise reduction applied to the signals within the analysis channels if the overall noise level is less than a predetermined minimum threshold.

In some examples, the sound amplitude of an audio signal that is above a noise floor (e.g., the predetermined minimum threshold) may be dynamically increased to compensate for the loss of amplitude that occurs as a result of the noise reduction described herein. The sound amplitude may be dynamically increased in any suitable manner as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
dividing, by a sound processing subsystem, an audio signal presented to an auditory prosthesis patient into a plurality of signals each representative of a distinct frequency portion of the audio signal and each contained within a distinct analysis channel included in a plurality of analysis channels;
determining, by the sound processing subsystem, a sound level of each signal included in the plurality of signals; and
setting, by the sound processing subsystem, an amount of noise reduction applied to each signal included in the plurality of signals in accordance with the determined sound level of each signal included in the plurality of signals.

2. The method of claim 1, wherein:
the determining comprises determining that a first subset of one or more signals included in the plurality of signals each have a sound level below a predetermined minimum threshold; and
the setting comprises minimizing the amount of noise reduction applied to the first subset of one or more signals.

3. The method of claim 2, wherein:
the determining comprises determining that a second subset of one or more signals included in the plurality of signals each have a sound level above the predetermined minimum threshold and below a predetermined maximum threshold; and
the setting comprises progressively increasing the amount of noise reduction applied to the second set subset of one or more signals in response to a progressive increase in the sound level of the second subset of one or more signals.

4. The method of claim 3, wherein:
the determining comprises determining that a third subset of one or more signals included in the plurality of signals each have a sound level above the predetermined maximum threshold; and
the setting comprises maintaining a maximum amount of noise reduction applied to the third subset of one or more signals.

5. The method of claim 3, further comprising setting, by the sound processing subsystem, the predetermined maximum threshold.

6. The method of claim 3, wherein the predetermined maximum threshold is substantially equal to a most comfortable current level ("M level") of the patient.

7. The method of claim 2, further comprising setting, by the sound processing subsystem, the predetermined minimum threshold.

8. The method of claim 2, wherein the predetermined minimum threshold is substantially equal to a threshold current level ("T level") of the patient.

9. The method of claim 2, wherein the predetermined minimum threshold is substantially equal to an ambiance sound level associated with the patient.

10. The method of claim 1, wherein the setting is performed in accordance with a mapping function that defines a mapping relationship between the sound levels of the signals to current levels of electrical stimulation representative of the signals.

11. The method of claim 1, wherein the setting is performed by decreasing a slope of a mapping function that defines a mapping relationship between the sound levels of the signals to current levels of electrical stimulation representative of the signals.

12. The method of claim 11, wherein the decreasing of the slope of the mapping function comprises increasing an input dynamic range ("IDR") associated with the mapping function.

13. The method of claim 11, wherein the decreasing of the slope of the mapping function comprises increasing a threshold current level ("T level") associated with the mapping function.

14. The method of claim 1, wherein the setting is performed in accordance with one or more operations performed by a noise reduction module included in the sound processing subsystem.

15. A method comprising:
dividing, by a sound processing subsystem, an audio signal presented to an auditory prosthesis patient into a plurality of signals each representative of a distinct frequency portion of the audio signal and each contained within a distinct analysis channel included in a plurality of analysis channels;
determining, by the sound processing subsystem, a noise level of each signal included in the plurality of signals; and
dynamically adjusting, by the sound processing subsystem, an amount of noise reduction applied to the signals in accordance with the determined noise level of each signal included in the plurality of signals, the dynamically adjusting configured to minimize the amount of noise reduction applied to each signal included in the plurality of signals that has a noise level less than a predetermined minimum threshold.

16. The method of claim 15, wherein the dynamically adjusting is performed by decreasing a slope of a mapping function that defines a mapping relationship between the sound levels of the signals to current levels of electrical stimulation representative of the signals.

17. The method of claim 15, wherein the predetermined minimum threshold is substantially equal to a threshold current level ("T level") of the patient.

18. The method of claim 15, wherein the predetermined minimum threshold is substantially equal to an ambiance sound level associated with the patient.

19. A system comprising:
a frequency analysis facility configured to divide an audio signal presented to an auditory prosthesis patient into a plurality of signals each representative of a distinct frequency portion of the audio signal and each contained within a distinct analysis channel included in a plurality of analysis channels; and
a noise reduction facility communicatively coupled to the channel facility and configured to
determine a sound level of each signal included in the plurality of signals, and
set an amount of noise reduction applied to each signal included in the plurality of signals in accordance with the determined sound level of each signal included in the plurality of signals.

20. A system comprising:
a frequency analysis facility configured to divide an audio signal presented to an auditory prosthesis patient into a plurality of signals each representative of a distinct frequency portion of the audio signal and each contained within a distinct analysis channel included in a plurality of analysis channels; and
a noise reduction facility communicatively coupled to the channel facility and configured to
determine a noise level of each signal included in the plurality of signals; and
dynamically adjust an amount of noise reduction applied to the signals in accordance with the determined noise level of each signal included in the plurality of signals, the dynamic adjustment configured to minimize the amount of noise reduction applied to each signal included in the plurality of signals that has a noise level less than a predetermined minimum threshold.

* * * * *